United States Patent [19]

Wang et al.

[11] 4,392,044
[45] Jul. 5, 1983

[54] METHOD FOR DETECTING WHETHER DISSIMILAR METALS ARE BEING WELDED

[75] Inventors: Teh P. Wang, No. Caldwell; Elmer J. Korn, Bloomfield, both of N.J.

[73] Assignee: Amax Inc., Greenwich, Conn.

[21] Appl. No.: 251,767

[22] Filed: Apr. 7, 1981

[51] Int. Cl.³ .............................................. B23K 31/00
[52] U.S. Cl. .................................. 219/118; 219/109; 219/137 R; 228/104; 324/71.1
[58] Field of Search ........... 219/130.01, 137 R, 56.22, 219/109, 118; 324/71 R; 228/103, 104; 29/573, 574

[56] References Cited

U.S. PATENT DOCUMENTS 2,790,656 4/1957 Cook .................................. 219/118
3,737,982 6/1973 Calhoun et al. ..................... 29/573

Primary Examiner—C. C. Shaw
Attorney, Agent, or Firm—Roland T. Bryan

[57] ABSTRACT

A method for detecting whether dissimilar metals or alloys are being welded together is disclosed. Metals or alloys are welded together and electrical leads connected to a multi-purpose potentiometer or a voltmeter contact each metal at points heat conductively remote from the weld. The arrangement performs as a thermocouple with the weld acting as the "hot junction" and the contact points remote from the weld being at substantially ambient temperature, and acting as the "cold junction." According to the thermoelectric laws, if the metals are dissimilar, a current and EMF result provided that the hot junction and the cold junction are at different temperatures. If the metals are similar, no signal is generated. The potentiometer or the voltmeter detects whether any electrical signal is present. In the same manner, an unknown metal may be positively identified by welding it to different reference metals until no signal is generated.

12 Claims, 2 Drawing Figures

METHOD FOR DETECTING WHETHER DISSIMILAR METALS ARE BEING WELDED

BACKGROUND OF THE INVENTION

The present invention relates to a method for detecting whether dissimilar metals are being welded together. More particularly, the invention relates to a method for detecting whether dissimilar metals are being welded together which uses the principles of thermocouples and thereby provides a simple, quick, inexpensive and accurate means of eliminating metal mix-up via welding.

In metal processing industries, metal coils are welded together during processing to save set-up time in wire drawing and to meet minimum finish coil weight requirements, among other reasons. Typically, the identities of the two coils to be joined are kept by tags or labels attached to the coils. Wrong materials, however, are sometimes joined together due to mislabeling or due to other human errors. The mistaken joining of dissimilar metals results in costly rejection by customers and possible products liability damage suits by consumers. Thus it is evident that a simple, quick, inexpensive and accurate means for eliminating metal mix-up via welding has long been needed and is most desirable in the metal processing industries.

Various methods for the identification of metals exist in the prior art, but none offers all the advantages of the present invention. For example, chemical analysis can provide identification of a metal but it is both time consuming and expensive. Thermoelectric devices do exist for metal identification. However, one device requires cutting up samples of the metals for testing them in an electric furnace versus known metal or alloy standards. Another device involves the measurement of thermal electromotive force (EMF) of the unknown metal versus a copper beryllium alloy probe at about 350° F., a temperature sometimes too low for distinguishing the difference between metals having similar EMF's at 350° F. or below. Clearly the prior art does not provide a simple, quick, inexpensive and accurate means for eliminating metal mix-up.

It was recognized by the inventors that a weld joint is indeed the thermocouple bead, or hot junction, of a thermocouple. By using the Thermoelectric Law of Intermediate Metals as cited in *Perry's Chemical Engineers' Handbook*, 4th Ed., N.Y. McGraw-Hill Book Co., 1963, p. 22-6, which states:

"If in any circuit of solid conductors the temperature is uniform from any point P through all the conducting matter to a point Q, the algebraic sum of the thermoelectromotive forces in the entire circuit is totally independent of this intermediate matter and is the same as if P and Q were put into contact.";

the inventors recognized that the electrical connection of the metals at a point remote from the weld which is at substantially ambient temperature could act as the cold junction. Thus, if the metals to be joined together are of different materials, an EMF will develop. This EMF and the resulting thermoelectric current can be detected readily by a properly connected multipurpose potentiometer, an ammeter, or a voltmeter. However, if the metals to be joined are of identical materials, no EMF will be created as the Thermoelectric Law of the Homogeneous Circuit requires that an electric current cannot be sustained in a circuit of a single homogeneous metal, however varying in section, by the application of heat alone.

A quick and inexpensive method for detecting whether dissimilar metals are being welded together is provided, and includes the steps of welding the metals together, and contacting each metals at point heat conductively remote from the weld with electrical leads connected to a potentiometer. This arrangement forms a thermocouple with the weld bead as the hot junction, and the remote contact points at substantially ambient temperature as the cold junction. If the metals are dissimilar, an EMF and electrical current result and may be detected by the potentiometer. If the potentiometer indicates that no signal is generated, the welded metals are identical.

By a similar method using the same principles, an unknown metal may be positively identified. The unknown metal is welded to different known reference metals until no signal is generated.

It is therefore an object of this invention to provide a method for detecting whether dissimilar metals are being welded together, thereby eliminating costly rejections and products liability damage suits by the customers and ultimate consumers.

Another object of this invention is to provide a simple, quick, inexpensive and accurate method for eliminating metal mix-up via welding.

Another object of this invention is to detect whether dissimilar metals are being welded without having to cut the metals for testing.

Another object of this invention is to provide a method for the positive identification of an unknown metal.

These, and other objects and advantages of the invention will become more apparent from the detailed description and appended claims taken in conjunction with the accompanying drawings.

PREFERRED EMBODIMENT OF THE INVENTION

The present invention comprises a method for detecting whether or not two metals being welded together are dissimilar, wherein the metals are welded together, and electrical leads which are connected to a potentiometer contact each metal at points heat conductively remote from the weld. A thermocouple thereby is established with the weld as the "hot junction" and the electrical lead contact points, which are at substantially ambient temperature, as the "cold junction". If the metals are dissimilar, an EMF results, and a current flows through the circuit. The signal is detected by the potentiometer, thereby permitting the operator to cut off the wrong material at the weld. If no current or EMF is detected, the metals are identical, and the weld may be dressed.

Figure 1:
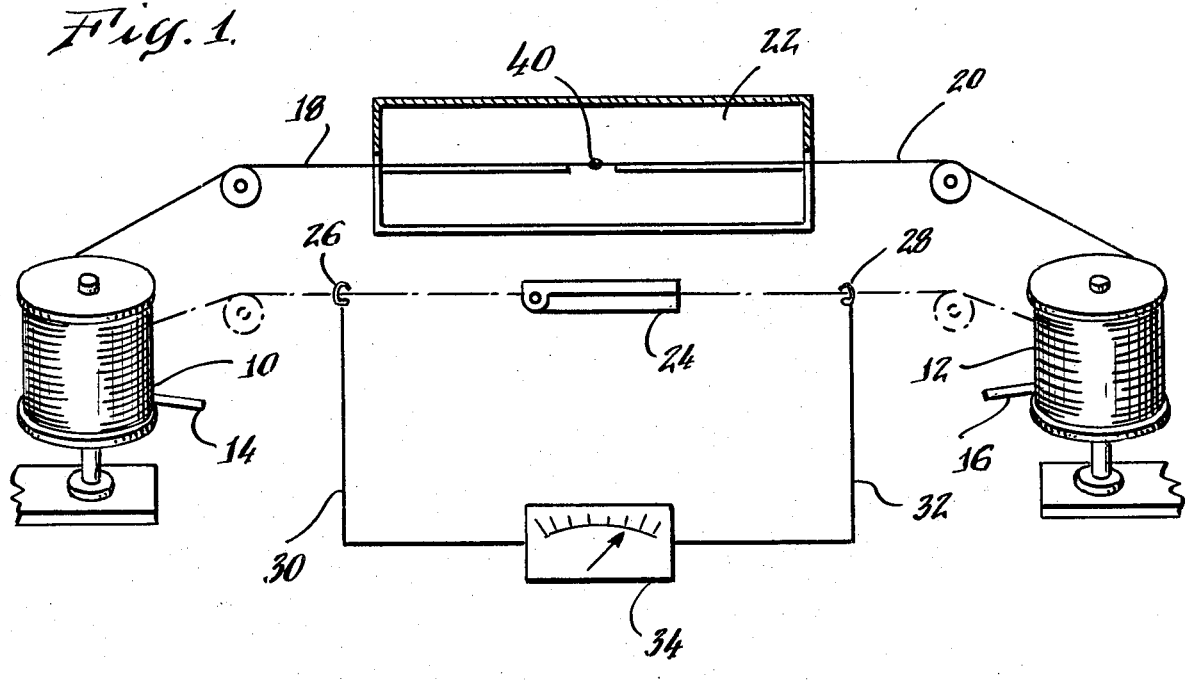
FIG. 1 is a diagrammatic view of the apparatus used in performing the method invention.

The invention is illustrated in FIG. 1 wherein metal coils 10 and 12 are to be welded together in order to meet minimum finish coil weight requirements. The coils have tags 14 and 16 which are used to identify the coils. The end piece of metal coil 10 is designated 18 and the end of metal coil 12 is designated 20. Metal ends 18 and 20 are supported by the welder 22, or by other suitable means.

Non-conductive clamp 24 is about one foot in length and is placed parallel to welder 22. It is positioned to receive and clamp the to-be-welded section of metals 18 and 20. In line with non-conductive clamp 24 and parallel to metals 18 and 20, are conductive clamps 26 and 28 which are attached to the test leads 30 and 32 of the meter 34. Conductive clamps 26 and 28 are positioned and formed to receive metals 18 and 20 and to contact said metals 18 and 20 at points heat conductively remote from their welding ends. Those skilled in the art will appreciate that the type of metal, its thickness, and the temperature and manner of welding will all the determinative of what distance is heat conductively remote so as to generate a detectable EMF or current.

Optimally, the cold junction points, where the test lead clamps 26 and 28 contact the metals 18 and 20, should be at the same temperature as each other and at a much cooler temperature than the hot junction weld point. Typically, if metals 18 and 20 are contacted by clamps 26 and 28 at points one or more feet from the welding ends, the contact points will be at substantially ambient temperature and will be sufficient to act as the cold junction. The conductive clamps 26 and 28 have copper wire test leads 30 and 32 which connect to a voltmeter 34. The voltmeter 34 preferably has a digital readout, but any indicating meter will suffice.

Figure 2:
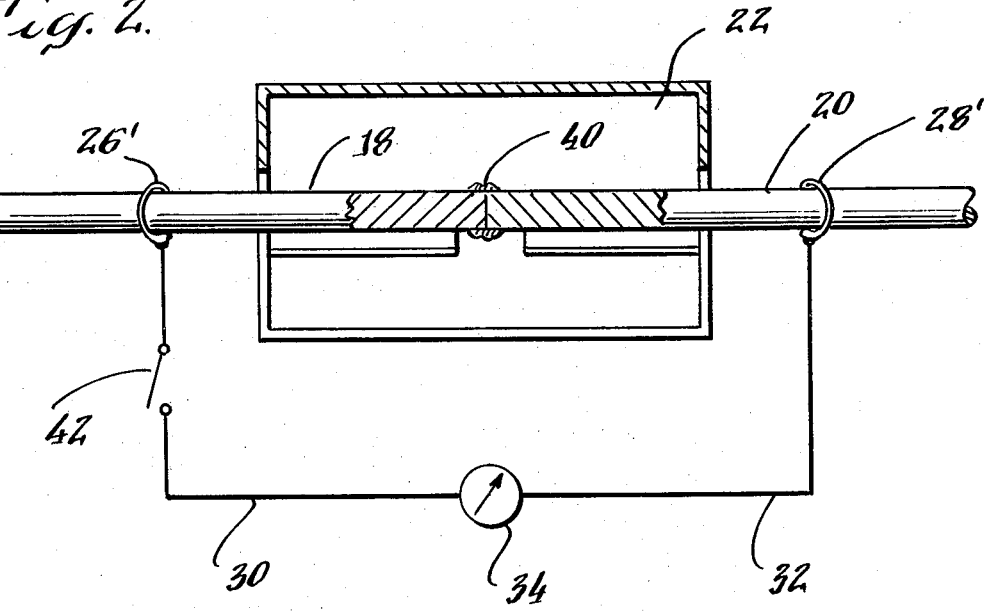
FIG. 2 is a diagrammatic view of an alternate apparatus used in performing the method invention.

An alternative embodiment of the invention is seen in FIG. 2 where metals 18 and 20 are supported by welder 22. Conductive flexible clamps 26' and 28' are positioned and formed to stand clear of metals 18 and 20 until said metals are positioned for welding, and to clamp over metals 18 and 20 before welding. In this embodiment the conductive flexible clamps 26' and 28' are positioned to contact said metals 18 and 22 at points that are heat conductively remote from their welding ends. Again the test leads 30 and 32 are as described above with respect to FIG. 1, except lead 30 is interrupted by switch 42.

In operation, tags 14 and 16 are checked to make sure that the metal coils 10 and 12 are identical. Metal ends 18 and 20 of coils 10 and 12 are placed in juxtaposition on welder 22 and prepared for joining by welding. Voltmeter 34 is turned on, and metals 18 and 20 are welded, forming weld bead 40. The manner of welding is immaterial, but often a butt welder is used for these purposes. The welded area, including metals 18 and 20, is quickly removed from the welder 22 and is clamped in non-conductive clamp 24 with weld bead 40 at the center. Metal 18 is clamped by conductive clamp 26, and metal 20 is clamped by conductive clamp 28. This operation must be completed within a reasonable time after welding so that the weld bead 40 will retain its "hot junction" characteristics. While the completion time varies with the metal, its thickness, and the manner of welding, typically, if the operation is not accomplished within fifteen seconds after welding, weld 40 should be cut off, and the welding and clamping procedures repeated. Fifteen seconds is chosen because, for example, it takes about 20 seconds for a weld bead of 0.032 inches in diameter at 2600° F. to cool to ambient temperature. Since the invention will not work with the "hot junction" at ambient temperature, the welding and clamping procedure must be repeated. Alternatively, the weld bead 40 may be reheated by any suitable means so that it can act as the hot junction. After clamping, the digital voltmeter 34 is viewed. If the voltmeter 34 is negligible, the metals are substantially identical, and the weld may be dressed. Otherwise, the metals are different and the weld will be broken. Of course, the EMF generated is a function of the particular metals being welded and the temperature difference at the hot and cold junctions at the time of detection. Generally, however, an EMF of 0.5 millivolts or less is considered negligible if detection occurs within fifteen seconds of welding.

Alternatively, tags 14 and 16 are checked to make sure that the metal coils 10 and 12 are substantially identical. As seen in FIG. 2, metal ends 18 and 20 of coils 10 and 12 are placed in juxtaposition on welder 22 and are prepared for joining by welding. Conductive flexible clamps 26' and 28', positioned at points heat conductively remote from the welding ends of metals 18 and 20, clamp said metals 18 and 20. Attached to said clamps 26' and 28' are copper wires 30 and 32 which connect to the voltmeter 34, copper wire 30 by way of open switch 42. The voltmeter 34 is turned on, and the metals 18 and 20 are electrically butt welded forming weld bead 40. Immediately after the welding is completed, switch 42, which had been kept in the open position, is closed. Switch 42, while open, acts to electrically insulate the alternating current electric welder circuit from the direct current thermoelectric circuit. Switch 42 should not be closed until the welder circuit is turned off. Otherwise, electrical interference would occur rendering the invention ineffective. However, if the weld is accomplished by suitable non-electrical means, switch 42 may be kept in the closed position. After welding, voltmeter 34 will indicate whether an EMF is present. If the voltmeter reading is less than or equal to 0.5 millivolts, the metals are substantially identical, and the weld my be dressed. Otherwise, the metals are different, the weld will be broken, and a proper new coil will be found.

For the positive identification of metals, either of the above procedures may be used. However, the identity of the metal coil 12 must be absolutely known. If, after welding, the reading on voltmeter 34 is negligible, the metal coil 10 is positively identified as substantially the same metal as coil 12. Otherwise the weld 40 must be broken. The identical procedure is then carried out using the metal end of another coil whose identity is different than coil 12, but is also absolutely known. This procedure is repeated in the same manner, with different coils until a negligible voltmeter reading occurs. In this way the unknown metal may be positively identified.

It is recognized that numerous variations may be made in the above described methods. For example, instead of using a voltmeter 34 to detect whether an electrical signal is present, a potentiometer or an ammeter may be easily used if properly connected. The ammeter, of course, would detect whether or not a thermoelectric current was generated.

Another variation would be to replace clamps 24, 26, and 28 with a bridge clamp which would be non-conductive where it would clamp the weld bead 40, but would have conductive ends which would clamp metals 18 and 20, and would be connected to leads 30 and 32. Of course, the conductor ends of the bridge clamp would be electrically insulated from each other.

Another variation would be to arrange end pieces 18 and 20 so that they would be in physical contact, not only at the weld, but at a point heat conductively remote from the weld. Copper wires 30 and 32, which connect to voltmeter 34, would be attached by clamps or other means at both the hot and cold junctions.

It should be appreciated that "metal" is being used in the specification and claims in a broad sense so that the invention applies to alloys as well.

All of these methods provide a simple, quick, inexpensive and accurate means for eliminating metal mix-up via welding. For example, it was desired to weld together metal coils tagged as Tophel (90 Ni/10 Cr) produced by AMAX, Inc. of Connecticut, so as to meet minimum coil weight requirements. The metal end pieces of the coil were placed on the electric welder and butt welded. The welded section was removed from the welder, and placed in the clamps within 6 seconds after the welding. The voltmeter indicated an EMF of 0.0 millivolts. Since the voltage was negligible the weld was dressed as the welded coils were substantially identical.

It was also desired to weld two other coils tagged as Tophel together. The metal end pieces were placed on the welder, welded, removed from the welder and clamped in a bridge clamp. The bridge clamping was accomplished in 6 seconds. The voltmeter indicated an EMF of over 20 millivolts. Since the voltage was not negligible the weld was broken as the metals were not identical. Since it was suspected that one of the coils might have been mistagged, and was actually the alloy Nial (95 Ni, 2 Al, 2 Mn, 1 Si), produced by AMAX, Inc. of Connecticut, a positive identification of the metal was carried out. The mistagged coil was welded to a known piece of Nial. Before welding, clamps, connected to the voltmeter by copper wire, had been clamped on the metal end pieces. Immediately after welding, the AC welding circuit was turned off and the DC circuit switch was turned on. The voltmeter indicated an EMF of 0.0 millivolts. Thus, the mistagged unknown metal coil was positively identified as Nial.

The invention thus makes use of the thermoelectric laws to provide a simple, quick, inexpensive and accurate method for detecting whether dissimilar metals are being welded together.

Further, a method for eliminating metal mix-up via welding is provided which does not require the cutting of the metals for testing. At the same time, a method for positive identification of an unknown metal is provided.

It should be understood by those skilled in the art that various modifications may be made in the illustrative embodiments of the present invention without departing from the spirit and scope thereof as described in the specification and defined in the appended claims.

What is claimed is:

1. A method for detecting whether two dissimilar metals are being welded together comprising the steps of:
    a. placing in juxtaposition the edges of two metals that are to be welded together;
    b. joining said metals by welding;
    c. contacting said metals with electrical leads which are electrically connected to a voltage or current sensing device at points heat conductively remote from the weld, while said weld is hot; and
    d. detecting whether an electrical signal is present, to reveal the similarity or dissimilarity of said metals.

2. A method for detecting whether two dissimilar metals are being welded together comprising the steps of:
    a. placing in juxtaposition the edges of two metals that are to welded together;
    b. contacting said metals at points heat conductively remote from where they are to be welded with electrical leads which are electrically connected to a voltage or current sensing device;
    c. joining said metals by welding; and
    d. detecting whether an electrical signal is present, to reveal the similarity or dissimilarity of said metals.

3. A method for welding substantially identical metals together comprising the steps of:
    a. placing in juxtaposition the edges of two metals that are to be welded together;
    b. joining said metals by welding;
    c. contacting said metals with electrical leads which are electrically connected to a voltage or current sensing device at points heat conductively remote from the weld, while said weld is hot;
    d. detecting whether an electrical signal is present, to reveal the similarity or dissimilarity of said metals; and
    e. dressing the weld if no signal, or a negligible signal is present.

4. A method for welding substantially identical metals together comprising the steps of:
    a. placing in juxtaposition the edges of two metals that are to be welded together;
    b. contacting said metals at points heat conductively remote from where they are to be welded with electrical leads which are electrically connected to a voltage or current sensing device;
    c. joining said metals by welding;
    d. detecting whether an electrical signal is present to reveal the similarity or dissimilarity of said metals; and
    e. dressing the weld if no signal, or a negligible signal is present.

5. A method for detecting whether two dissimilar metals are being welded together, as recited in claims 1 or 2, wherein:
    said electrical leads contact said metals at points approximately one foot or more from the weld.

6. A method for detecting whether two dissimilar metals are being welded together, as recited in claim 5, wherein:
    said electrical leads are copper wires; and said metals are metal coils.

7. A method for detecting whether two dissimilar metals are being welded together, as recited in claim 6, wherein:
    said electrical leads have conductive clamps attached to their ends for contacting said metals; and
    said electrical signal is detected by a voltmeter, ammeter, or potentiometer.

8. A method for detecting whether two dissimilar metals are being welded together, as recited in claim 1, wherein:
    said contact between said electrical leads and said metals occurs within approximately 15 seconds of said welding.

9. A method for detecting whether two dissimilar metals are being welded together, as recited in claim 2, wherein:
    said metals are welded by an electric welder; one of said electrical leads is broken by a switch; and said electrical signal is detected by a voltmeter, ammeter, or potentiometer.

10. A method for detecting whether two dissimilar metals are being welded together, as recited in claim 1, further comprising:
   e. before step a., arranging the metals on a welder; and
   f. after step b., but before step c., quickly removing the welded section from said welder and clamping it firmly on a non-conductive clamp, with the weld approximately at the center.

11. A method for detecting whether two dissimilar metals are being welded together, as recited in claim 9 further comprising:
   e. before step a., arranging the metals on an electric welder;
   f. before step c., placing said switch in an open position, thereby insulating a direct current circuit containing said voltmeter from an alternating current circuit containing said electric welder; and
   g. immediately after step c., and before step d., closing off and breaking said alternating circuit, and placing said switch in a closed position to complete said direct current circuit.

12. A method for detecting whether two dissimilar metals are being welded together, as recited in claims 1 or 2, for the positive identification of one of the metals, where the other metal is a known reference metal, further comprising:
   e. cutting off said weld if a signal is generated;
   f. replacing said known reference metal with another known reference metal; and
   g. repeating steps a. through f. until no electrical signal is detected during step d.

* * * * *